United States Patent [19]

Jones et al.

[11] Patent Number: 5,307,137
[45] Date of Patent: Apr. 26, 1994

[54] TERRAIN IMAGING APPARATUS AND METHOD

[75] Inventors: Mark F. Jones, 6310 Rustling Way, San Antonio, Tex. 78249; James C. Lyman, Pipe Creek, Tex.

[73] Assignee: Mark F. Jones, San Antonio, Tex.

[21] Appl. No.: 851,870

[22] Filed: Mar. 16, 1992

[51] Int. Cl.$^5$ .............................. G01C 3/08
[52] U.S. Cl. .................................... 356/5
[58] Field of Search .................... 342/24; 356/5, 4

[56] References Cited

U.S. PATENT DOCUMENTS

| | | | |
|---|---|---|---|
| 2,496,639 | 2/1950 | Richardt, Jr. et al. | 342/24 X |
| 3,337,839 | 8/1967 | Nelkine | 342/24 X |
| 4,856,893 | 8/1989 | Breen | 356/5 |

Primary Examiner—Mark Hellner
Attorney, Agent, or Firm—Charles W. Hanor

[57] ABSTRACT

A terrain imaging apparatus and method for indicating to a user the location and distance of moving objects from a user. A transmitting means transmitts a coherent radiation beam to distant objects and receives back the coherent radiation beam reflected from the objects. A communicating means indicates the direction and distance of objects moving in that field relative to the user by determining the distances to the objects from the transmitting and receiving means and the direction in which the beam is directed to synthesize a vector field image of the terrain based on a set of direction measurements and corresponding range measurements and indicating the direction the user is facing relative to the terrain image.

8 Claims, 7 Drawing Sheets

TERRAIN IMAGING APPARATUS AND METHOD

BACKGROUND OF THE INVENTION

This invention relates to terrain imaging using coherent beam radiation. It is usable to detect short range objects and determine the movement of the objects. It can be used by a blind person to avoid running into obstacles. Law enforcement and security personnel can use it to detect the location and movement of persons which are not visible to the eye such as at night.

In the last several decades, several electronic techniques have been tried to develop methods to image the near field terrain of an area for circumnavigating through and around obstacles and for protection against intrusion of an area. These methods have suffered from a common problem of poor resolution and false information or images as a result of background objects moving, such as leaves blowing, birds flying or small animals.

One of the technologies employed for intrusion detection or for terrain imaging has been ultrasonics. An ultrasonic acoustical signal is transmitted into space is reflected from objects in the near field to the transmitter. By ascertaining the return signal level or by measuring the time delay, you can infer a range of the object from the transmitter to the receiver.

A primary problem with the ultrasonics is the very low resolution of distinguishing objects. This is a result of the difficulties in focusing the ultrasonic sound waves into a small beam that doesn't disperse. The relatively low resolution of an image by such a method makes it of less value to the user in trying to circumnavigate himself through an area of obstacles. When this method is used for intrusion detection, the low resolution is not the only problem. Ultrasonics is very susceptible to motion from blowing bushes, plants or small animals moving about. These objects, when in the field of view, tend to give a high number of false alarms. Other technologies have attempted to use light or microwave emissions to detect the presence of objects, but have relied largely on the return signal strength or on triangulation to determination what the range is to the reflecting objects. These methods of range determination suffer from low resolution since triangulation can only be used for a very near field. Signal strength is subject to other sources of errors, in particular, the type of target light hits and hence the amount that is reflected back.

The inability to resolve accurate ranges well as the azmith of those ranges have made these methods of limited value. Failure to use computational devices to interpret what image is generated has further reduced the effectiveness of these methods.

One type of light intrusion detection that has been used successfully and extensively is the photo-electric beam devices. These devices require some sort of an inflector that is the receiver at the end of a light beam to operate. This method has not been used for scanning but does not produce any accurate image of the surrounding terrain. Furthermore, this method does not provide range information about intrusions.

Methods of passive infrared emissions have also been used for intrusion detection and for a means to avoid obstacles. These methods do not provide good range information and provide no azmith information and do not generate good images.

Video based systems by their very nature provide a very high definition image. However, translating this image information into a format usable by the blind or by a computer is a problem of great complexity. While it is possible to use video systems for motion detection in an intrusion scenario, they are plagued by high false alarm rates since any change in light causes an alarm signal. This method generally requires a stable closed environment in which to work. Thus, a method that can provide moderate resolution image of only 2 dimensions provides a means that can easily be interpreted by computational methods or by the blind, who can only process a limited amount of stimuli, and interpret as an image.

An object of the invention to provide a method and apparatus which can be used by a blind person to ascertain obstacles and to indicate the location and movement of the obtacles.

Another object of the invention to provide a method and apparatus which can be used by any person at night to ascertain obstacles and to indicate the location and movement of the obtacles.

Another object of the invention to provide a method and apparatus which can be used to ascertain short range obstacles and to indicate the location and movement of the obtacles.

Another object of the invention to provide a method and apparatus which can be used to ascertain obstacles and to indicate the location and movement of the obtacles in security monitoring situations.

Other objects of the invention will be apparent from the specification and claims.

SUMMARY OF THE INVENTION

A scanning terrain imaging for generating a moderate resolution image of a simple format that is easily used by computing devices to monitor areas for motion or intrusion, or to provide an image that is easily reproduced mechanically for presentation to a blind person. An area is scanned to measure range and azimuth sets of data, which constitutes a set of vectors. A vector field image of the surrounding objects is formed. This image may be simplified means of calculation for mechanical representation as an aid to blind people circumnavigating their way around obstacles in their environment. These vector field images may also be used to detect the occurrences of motion in applications of security and law enforcement. Images are compared by computing devices to determine changes in images, which may then be resolved into true objects in motion. Subsequent comparisons permits computing devices to track those moving objects and based on their motion, make decisions as to the nature and intent of those moving objects.

DESCRIPTION OF THE PREFERRED EMBODIMENTS

The system generates an image of the terrain using range vectors derived from a laser radar. This image may be used to navigate around obstacles or detect motion of objects occurring in the image field of view.

Figure 1:
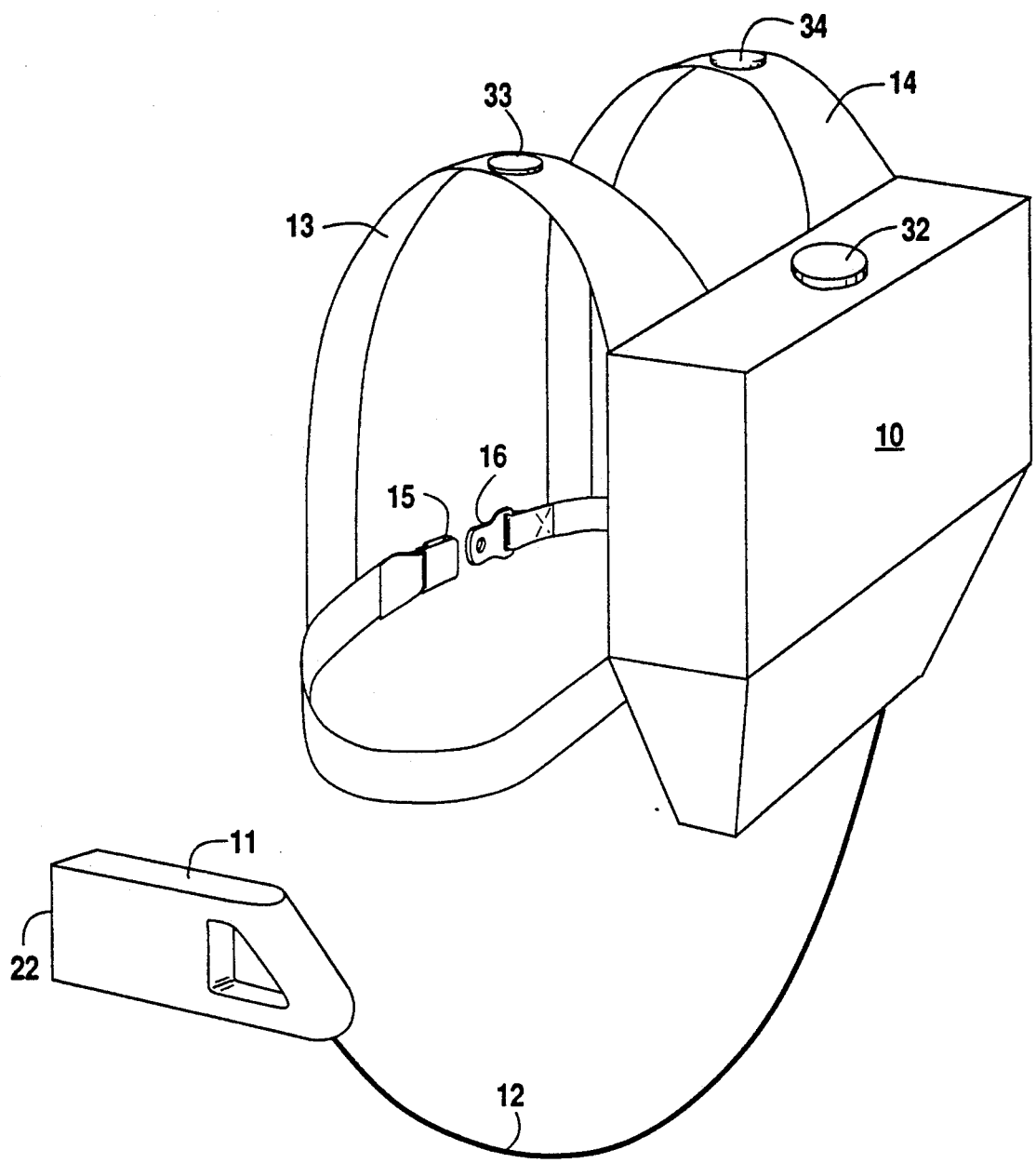
FIG. 1 shows a perspective view of the backpack embodiment of the invention including the hand held scanner.
Figure 2:
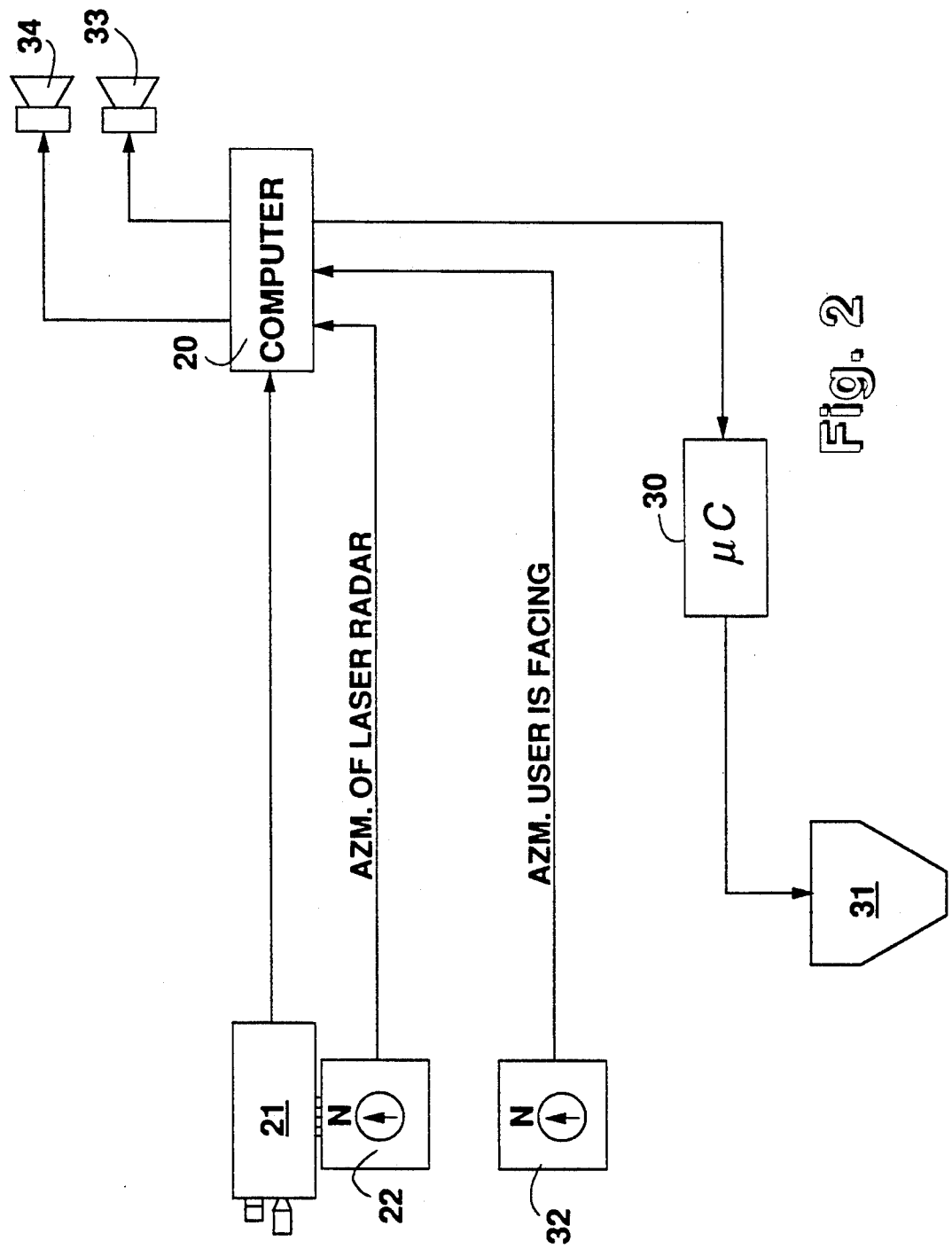
FIG. 2 shows a diagrammatic flow chart for the backpack embodiment of the invention including the hand held scanner.

The backpack 10 in FIG. 1 and FIG. 2 contains a computer 20, the power supply and a micro-controller 30. A person wears the backpack 10, and would have the vibrator matrix back plate 31 in FIG. 3 against and in contact with his back. The radar device 11, in FIG. 1, is held by the user in his hand.

Referring to FIG. 1, there is the hand-held radar device 11. It is connected by cord 12 to the backpack 10. Looking at FIG. 2, the hand-held laser radar, 21, emits a laser beam that is a coherent and non-diverging beam. When an object is in front of the beam, it reflects a portion of that beam that in turn is received by a lens which focuses the beam on an electronic sensor. The hand held radar device also contains a remote electronic compass 22. It could be on the top or bottom as long as it's not around any significant metallic objects.

The hand held unit would be measuring ranges of generally not more than 30 to 40 feet, since the user may not be able to use range information beyond that distance. This requires a laser of only 1 to 3 milliwatts, which is a low enough power level that its use is safe eye protection.

The user sweeps the radar device across the area by hand, directing it's beam to the area where he wants the image. The transmitted signal from hand-held laser radar 21 has a tone modulated on it that is retained by the received signal. The tone on the received light beam is converted into an electronic signal and compared with the local reference to get a phase difference in tones. This phase difference thereby deduces what the range is to the object. This range information is fed into the computer. The radar device has the light beam source which is a solid state laser.

The backpack in FIG. 1 also contains a local electronic compass 32 for the user. There are audio devices 33 and 34 which give a range coded tone, or an over-scan alarm. The audio devices 33 and 34 in FIG. 2 are connected to the computer, 20. The audio devices 33 and 34 are mounted on the backpack, straps 13 and 14 in FIG. 1. Backpack straps 13 and 14 with connectors 15 and 16 attach the backpack 10 to the user. In FIG. 2, the computer 20 is connected to the hand-held laser radar, 21 which has the remote electronic compass 22.

The computer takes the range and azimuth information from the scanning of the laser radar 21 and determines the zones in which these objects are located. The zones reflects a course block containing an obstacle. These zones related to the individual transducers on the vibrator matrix 31 of FIG. 3, on the backpack 10 in FIG. 1, which vibrate if there is an obstacle in that zone.

Figure 3:
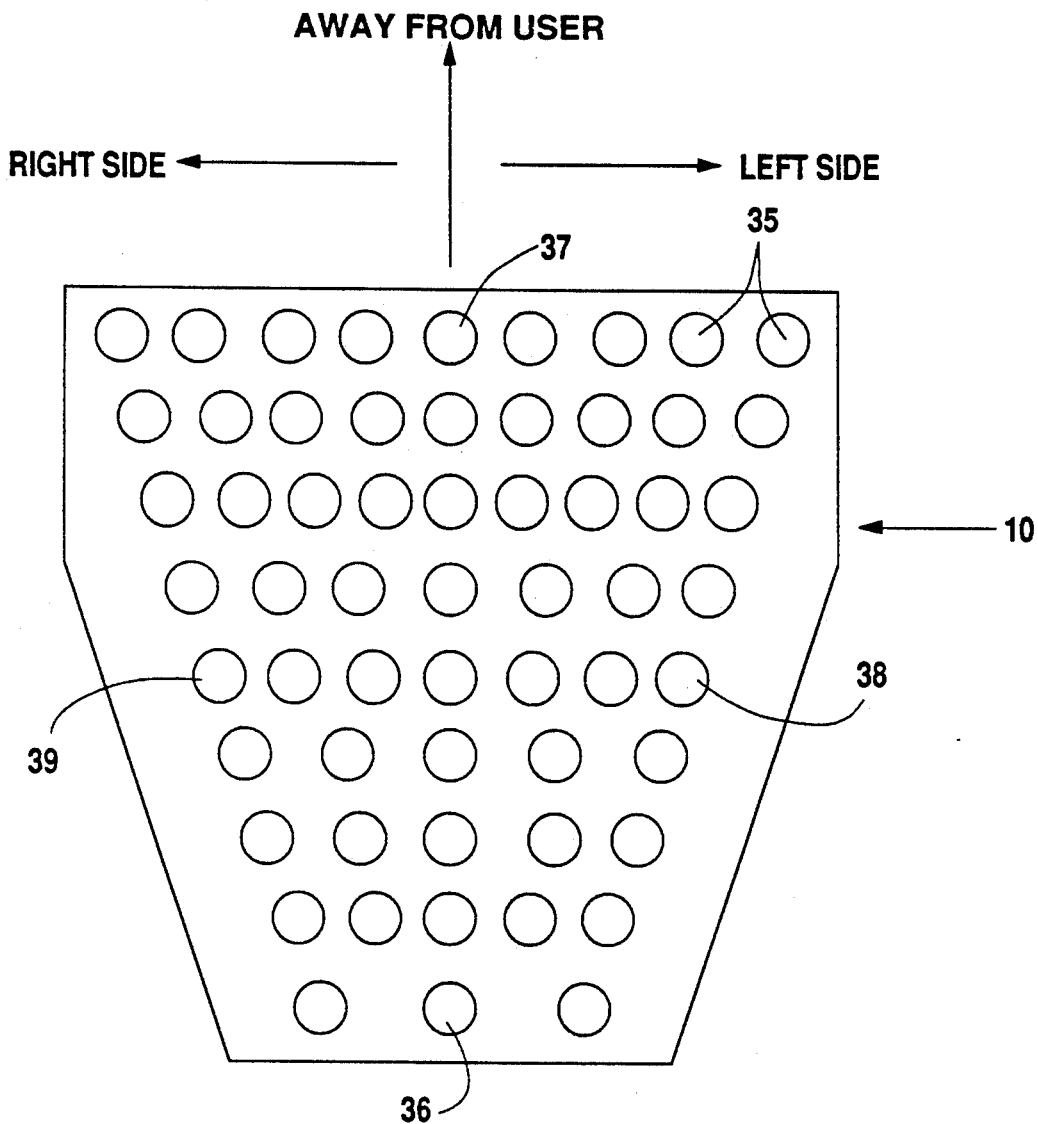
FIG. 3 shows the side of the backpack having the vibrating transducers that contact a user's back.

In sweeping, the user must maintain the sweep within the confines defined by the map on the back of the vibrator matrix back plate 31 of FIG. 3. The map is define by transducers 35 through 39. The computer calculates the angle that the user is sweeping with respect to the direction he is facing. When this angle exceeds the limits defined by transducers 38 and 39, of the vibrator matrix backpack 31, it sounds an over scan alarm on audio devices 33 and 34. The vibrator matrix 31 on the back forms a course image of the surroundings in front of the user.

A series of transducers are dispersed on the back side of the backpack as shown in FIG. 3. These transducers engage the back of the individual that is wearing the backpack 10 of FIG. 1. Each transducer of FIG. 3 would correspond to a distance from the user. Starting at the bottom, transducer 36 is nearest the user and going all the way up to transducer 37 would indicate the furthest distance from the user. Lateral transducers 38 and 39 would indicate the offset angle from the user that a range occurs.

Transducer 36 would indicate an object being closer to the user, while transducer 37 would indicate objects further away. Transducer 38 would indicate an object to the left of the user, while transducer 39 would indicate an object to his right. The transducers are electro-mechanical devices containing plunger-like device with a spring that can move back and forth in one direction through a coil. To activate, a pulsing current is passed through the coil at a rate equal to the resonance of the transducer. These transducer are much like a ringer on the older style telephones, and they lightly buzz the user when energized by the micro-controller.

The range from the hand-held laser radar 21 of FIG. 2 is used to control the pitch of a tone. This range encoded tone takes the proportional range voltage from the hand-held laser radar and gives a tone that is proportional to that range. Using this tone, the user can do a small scan and hear the range changing, thus making fine discriminations of range. The human ear is very accurate in its tone discrimination ability. Therefore, while the backpack is giving range information with a resolution of 3 to 5 feet, the tone would resolve range within a few inches. A user could thus ascertain stair steps or where a doorway is located in a wall.

For the blind, this system would tell that objects are in front of the user and if he is about to come in contact with them. It would also tell the user if these objects were moving objects or stationary objects and what their relative position was to him. The user can thus determine how much caution he must exercise and whether he is safe from them.

Figure 5:
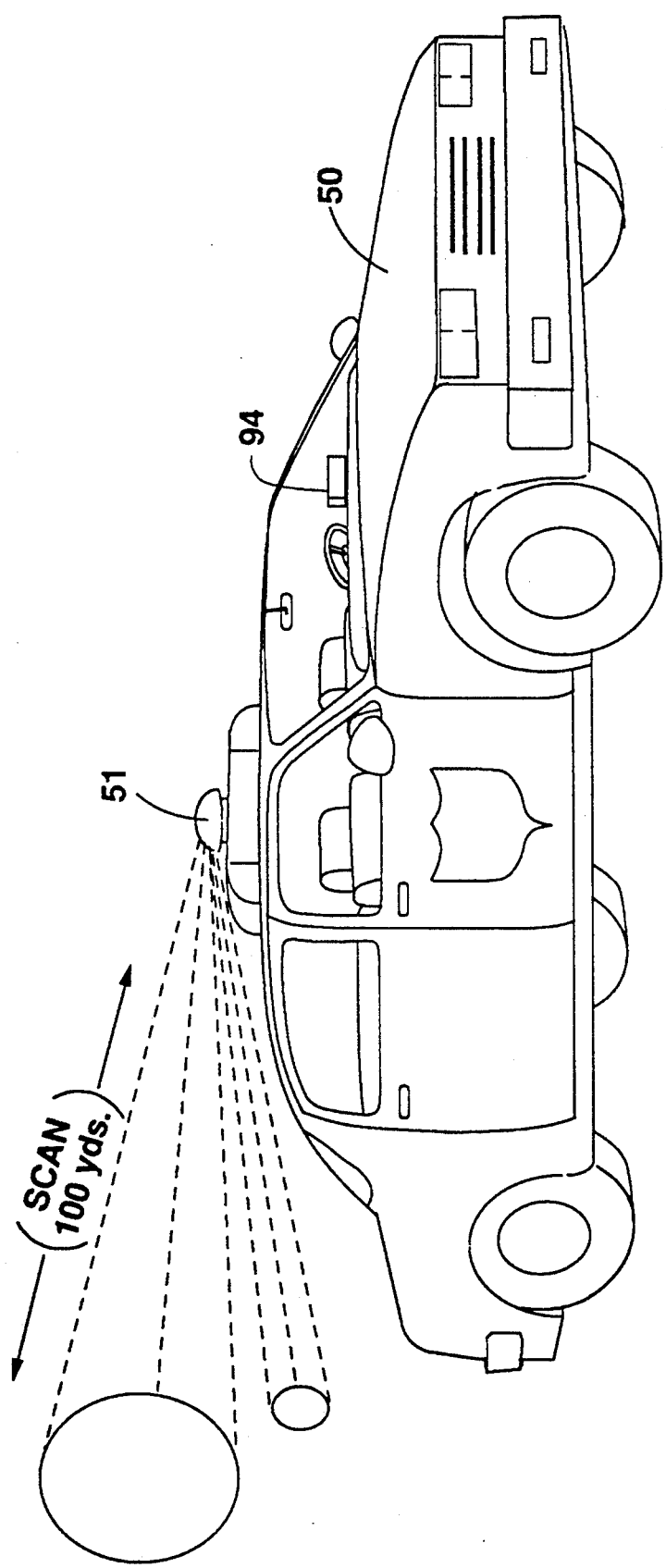
FIG. 5 shows motor vehicle including the vehicle mounted embodiment of the invention.

Vector field images may also be used for the detection of motion within the viewing field. A portable or vehicle mounted unit could be used by police, military, security or anyone that wanted to detect moving objects out in an area in shown in FIG. 5. An example would be a police car, 50. The car would include a laser search and detecting system, which uses a scanning module 51 on top of the vehicle to allow the vehicle to scan up to 100 yards. Inside the vehicle there would be a CRT Display 94 for an operator to see an image of the surrounding terrain.

The system detects motion by generating a reference image of range-azmith vectors using a laser radar.

This reference image is generated from the range-azmith vectors using a conventional digital computer. After capturing a reference to use as a baseline image, the system will continue to monitor the scanning of the laser radar. The system compares each new vector to determine if a change in range has occurred. If a change occurs, the computer considers this to be a moving target and tracks that target. Using the track of an object, the system determines if movement is towards or away from a user, thereby determining whether the moving object is a threat to the user.

Figure 4:
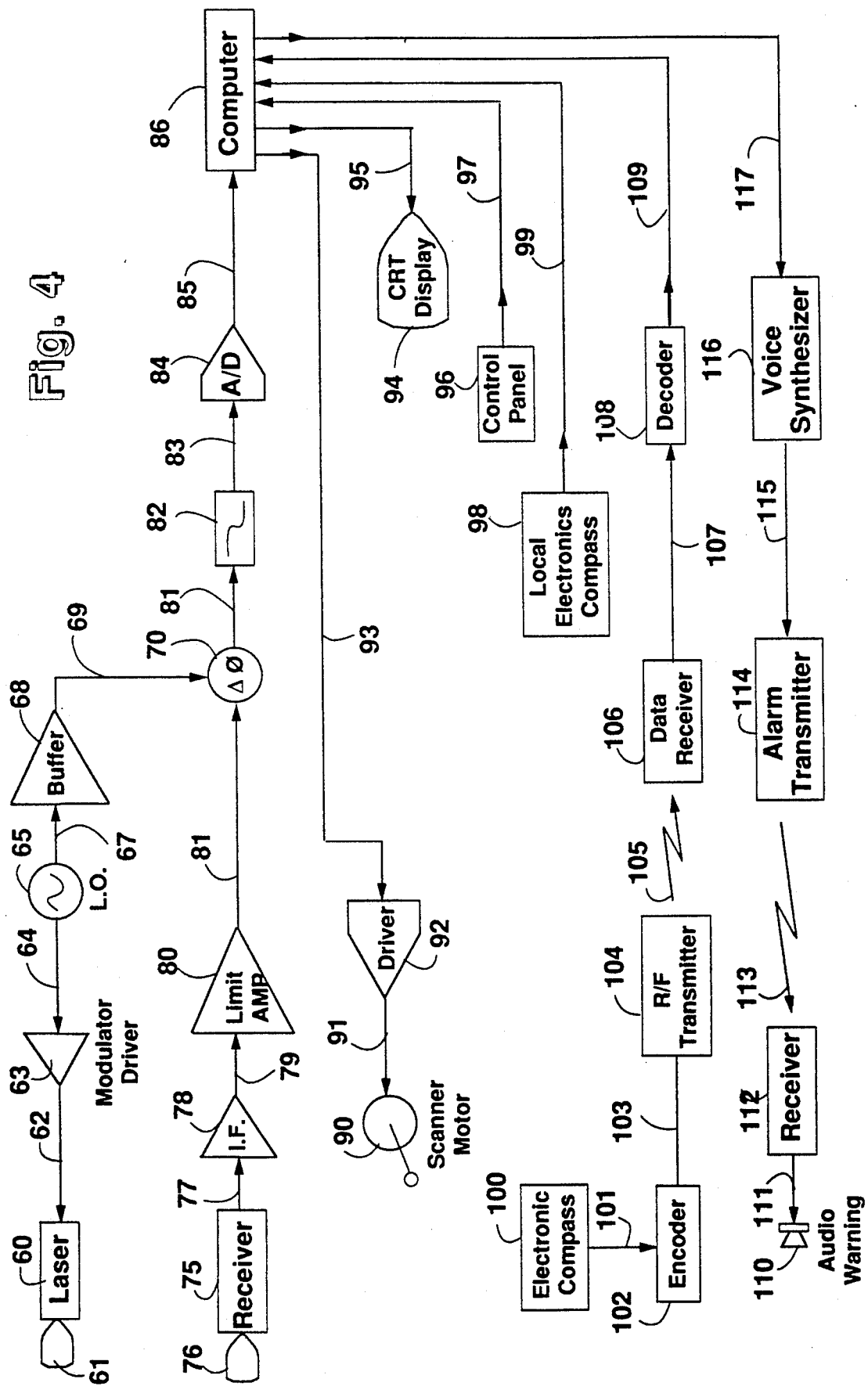
FIG. 4 shows a diagrammatic flow chart for the vehicle mounted embodiment of the invention.

FIG. 4 shows a block diagram of the particular device and how it operates. The transmitting unit includes a laser 60 which is a solid state laser with 3 milliwatts or less of output. The laser lens 61 is mounted on the laser 60, which in turn is connected by connector 62 to the modulator driver 63.

The modulator driver 63 is connected by connector 64 to a local oscillator 65, which is connected by connector 67 to an impedance matching buffer 68, which is connected by connector 69 to a phase comparator 70.

The local oscillator 65 provides a constant signal which is fed through connector 64 to modulator driver 63. This provides the power signal necessary to modulate the laser beam through connector 62, so that the laser 60 has an amplitude modulated light beam that is projected out the laser lens 61.

The local oscillator output is also sent to a buffer amplifier 68 through connection 67, this takes the amplitude of the local oscillator and translates it to an impedance that is compatible with the phase detector through connector 69.

Continuing with FIG. 4, the receiver 75 is used in connection with the laser system of 60 through 64 and has a receiving lens 76.

When the beam is transmitted down the range as a small coherent beam, and strikes a target or an object, a portion of that beam is reflected back and received by receiving lens 76.

The receiver 75 receives the light beam transmitted from the laser lens 61 by the receiving lens 76. The receiver 75 takes this light modulated light beam and converts it to an electrical signal that has the modulated tone on and is now shifted in phase because of the time of travel from the laser lens 61 to the reflecting object and back to receiving lens 76.

The electrical signal of the modulated tone is transmitted through connector 77 to an IF amplifier 78. The IF amplifier 78 is connected to line 79 to a limiting amplifier 80 which is connected by connector 81 to the phase comparator 70. The amplified electrical signal goes by connector 79 to the limiting amplifier 80 which limits the amplitude of this received tone signal to a constant amplitude without corrupting any of the phase information. It is important that the limiting amplifier 80 doesn't corrupt the phase information, otherwise, the range would vary with both the light level received and the range. The output of the limited amplifier goes through connector 81 to the second input of the phase comparator 70.

The phase comparator 70 measures the difference in phase of the electrical signals from connectors 69 and 81. The phase difference is represented by a proportional DC voltage at connector 81. Connector 81 goes to a low pass filter 82, which is connected by connector 83 to an analog to digital to converter 84. The analog to digital converter 84 is connected by connector 85 to the computer 86. This DC voltage is passed through connector 81 to a low pass filter, 82, which filters out any noise in that range measurement. Then it passes through connector 83 to the analog to digital converter 84, where the voltage representing range, is converted to a binary digital representation. This digital number is also proportional to the range information, and is compatible with the computer 86. The binary digital range is fed to computer 86 through connector 85, thus providing the range information of the object to the laser radar.

Scanner motor 90 of FIG. 4 is connected through connector 91 to driver 92. Driver 92 takes the digital information from the computer specifying the angle the laser is to point. The scanner motor 90 is physically connected to the laser 60 and receiver 75 to control the direction the laser 60 and receiver 75 sweeps. The driver 92 provides the energy to drive the scanning motor 90 which is a stepper type motor. The driver is connected by connector 93 back to computer 86. Since the computer directly controls and points the direction of laser 60 and receiver 75, the computer always knows the azmith where the radar is pointing. This display provides a visual image of the vector field image to the user.

The control panel 96 is the systems interface where the user would turn the system on and off, set limits for the scan, and any other control operations that would be required by the device. The control panel 96 is connected through connector 97 to the computer 86.

Local electronic compass 98 is an electronic compass that is connected to the unit. Since the computer knows the angle that the radar is pointing with respect to the unit, it uses local electronic compass 98 to establish the true pointing position of the laser radar. The local electronic compass 98 connects via connector 99 to computer 86.

Electronic Compass 100 is connected through connector 101 to an encoder 102, connected through connector 103 to a RF transmitter 104. A radio transmission link 105 sends back azmith data to a data receiver 106, which is connected through connector 107 to a decoder 108 which is connected through link 109 to the computer 86.

The electronic compass 100 of FIG. 4 is attached to the user when he is away from the unit. A bearing is generated by the electronic compass 100 that relates the direction the user is facing with respect to the magnetic north. This bearing information is encoded into a digital format by the encoder 102, which is connected by connector 103 to the RF transmitter 104. The digitally encoded azmith is then transmitted by the radio link 105 and received by the data receiver 106. It is connected by connector 107 to the decoder 108 which takes the encoded azmith information and converts it into a binary number usable by a computer. Connector 109 connects to computer 86, so that it reads the azmith direction from decoder 108 by connector 109. Computer 86 now has the direction the user is facing relative to the vector field image.

By comparing the user's azmith from electronic compass 100 and the azmith that the computer 86 reads from the local electronic compass 98, the computer is able to ascertain the position of the user's back with respect to moving objects. Using this (a) position information, (b) direction the moving objects are moving with respect to the user's back; and (c) the moving object's velocity, computer 86 determines threats to the user.

Audio warning device 110 is connected by a line 111 to a receiver 112, which has a radio connection 113 to a transmitter 114. The transmitter 114 is connected with connector 115 to a voice synthesizer 116, which is connected through connector 117 to the Computer 86.

Figure 6:
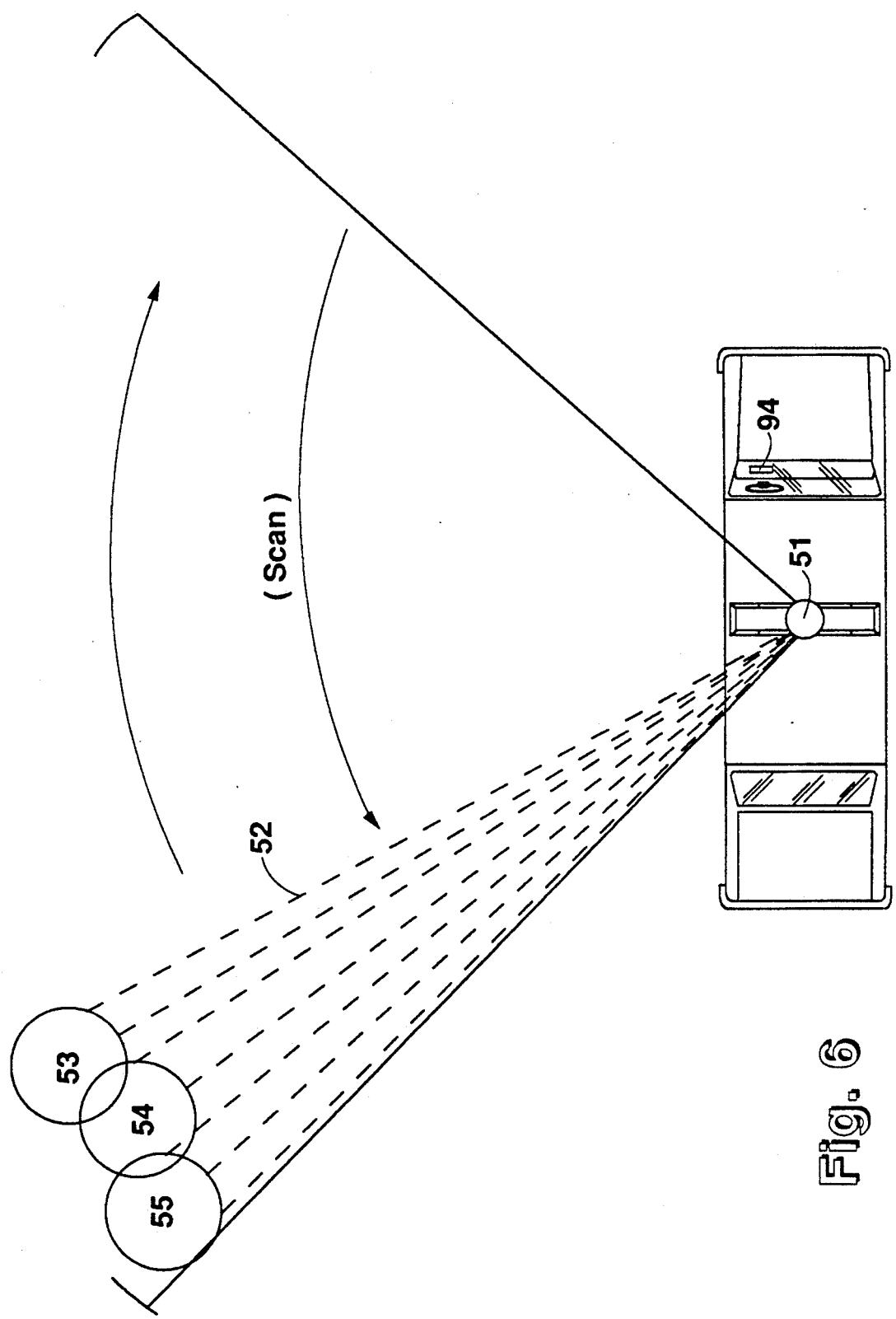
FIG. 6 shows a representation of the operation of the motor vehicle including the vehicle mounted embodiment of the invention.

The computer initially takes a full scan from the laser radar which includes components 60 through 85 and creates an image in its memory of the surrounding objects as a set of vectors of azmith and range as represented in FIG. 6 by laser beams 52. After creating this baseline reference image, the system continues to monitor the scan of the laser radar. The system compares each new azmith-range vectors with the reference vector having the same azmith. If differenct, the computer considers that azmith to be a target and starts following or tracking it to ascertain what direction it is moves and at what speed. The computer 86 in FIG. 4 is connected to voice synthesizer 116 by connector 117. The computer 86 synthesizes a warning message using voice synthesizer 116, which describes the threat, where it is coming from, and how threatening it is expected to be. By connector 115, the voice synthesizer modulates the alarm transmitter 114 with this audio message which is transmitted over radio connector 113 to receiver 112. The audio message is demodulated and sent by connector 111 to audio warning 110 where a spoken message is projected in the user's ears specifying what the threat is and its severity.

Based on the direction the target is moving and the velocity it is moving, Computer 86 makes a determination as to whether it is a threat to the user, and if a threat, to what degree. The criteria is based on the direction the user is facing and hence what direction his back is relative to the target that is moving and whether this target is moving towards or away from the user's back.

How fast the target is moving is then considered to determine the degree of that threat. The faster it is moving towards the User's back, the higher the degree of threat. Upon ascertaining that this is a threat and assigning some level of threat measure, an audio warning is given to the user.

The scanning module 51, as shown in FIG. 6, would send out laser beams 52, which would reflect back off the objects 53, 54 and 55 to give the relative distance of these things. The CRT Display 94 inside the vehicle would give an image formed by range measurements of the objects detected.

Figure 7:
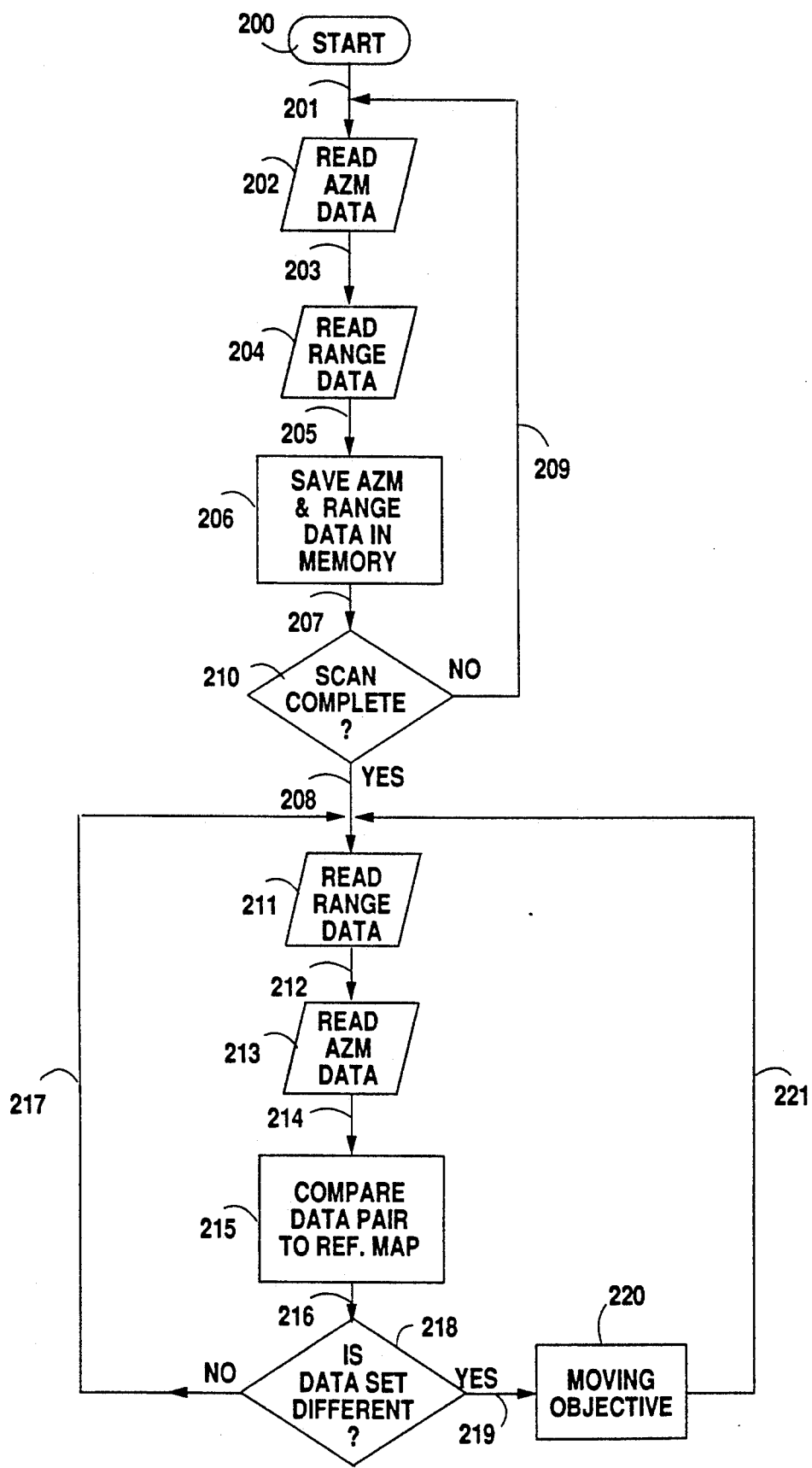
FIG. 7 shows a diagrammatic flow chart for the operation of the invention.

Referring to FIG. 7, the execution of the program begins at START 200. This module of the program does any initializing of the system, and sets any constants or variables used later in the program. After completion, the program goes via connector 201 to READ AZM DATA 202. In this module, the computer resolves the direction the Laser Radar is pointing, with respect to a fixed reference. Next the program goes to READ RANGE DATA 204, via connector 203.

The range data, representing the distance from the laser radar to a reflecting object, is read from the output of the laser radar. The program then goes via connector 205 to SAVE AZM & RANGE DATA IN MEMORY 206. The previously made range and azmith readings are saved in the computer's memory as a data set in an array. The program then goes to a decision via connector 207 to SCAN COMPLETE? 210 where the computer determines if a full scan has been made, by analyzing the azmith measurements. If the scan is not completed, then the program branches via connector 209 to READ AZM DATA 202 to repeat the process of reading new range and azmith data sets. This looping process, from 202 to 210, continues for the full defined area of scan and allows the computer to create a vector image of the surrounding area as an array of range-azmith data sets.

When the computer determines the scan in completed in SCAN COMPLETE? 210, then the program continues via connector 208 to READ RANGE DATA 211 to start looking for changes in the position of any surrounding objects. In READ RANGE DATA 211, the computer reads the range data from the laser radar. The program then continues via connector 212 to READ AZM DATA 213, to read the azmith of the laser radar that corresponds to the range of READ RANGE DATA 211. With the new range-azmith data set, the program continues via connector 214 to COMPARE DATA PAIR TO REF. MAP 215. Using the previously created reference map, the program reads the reference range having the same azmith as the data set just made. The two ranges are then compared to determine if they are equal within some limits of tolerance. Using this comparison, the program goes via connector 216 to IS DATA SET DIFFERENT? 218, to make a decision for program branching. If the range has changed then the program branches via connector 219 to MOVING OBJECT 220. The program resolves the moving object in MOVING OBJECT 220 to determine if that object poses a threat based on (a) the direction the object is moving relative to the back of the user, (b) the speed that it is moving; and (c) by the distance from the user.

The program then continues via connector 221 to READ RANGE DATA 211, to continue the scan process. If the range has not changed, then the program branches to connector 217 back to READ RANGE DATA 211 to continue the scan process. Modules 211 through 220 constitute a continuous scan process.

The invention has been described in detail with particular reference to a presently preferred embodiment, but it will be understood that variations and modification can be effected within the spirit and scope of the invention.

We claim:

1. A method for imaging the terrain in an area surveyed by the user, comprising the steps of:

transmitting a coherent radiation beam to near objects and receiving the coherent radiation beam reflected from the objects;

measuring the distances to the objects from the transmitting and receiving means and the direction in which the beam is directed and synthesizing a vector field image of the terrain based on a set of direction measurements and corresponding range measurements to establish a reference point;

continually synthesizing vector field images of the terrain based on a set of direction measurements and corresponding range measurements and comparing each synthesize vector field image with the reference to determine those objects which are in motion and automatically selecting and tracking those objects which are indicated to be in motion to predict the near future positions of those moving objects;

continually determining the degree of threat which each moving object presents to the user, based on the distance of the moving object from the user, the direction of movement that each moving object has relative to the position of the user, and the direction that the user is facing and the velocity that each moving object is experiencing;

grading and ranking of multiple moving objects as to the degree of a threat each moving object presents to the user and determining which moving object presents the greatest and most immediate degree of a threat for the user; and communicating the direction and distance of objects moving in that field relative to the user, calculating the distances to the objects from the transmitting and receiving means and the direction in which the beam is directed and synthesizing a vector field image of the terrain based on a set of direction measurements and corresponding range measurements to indicate the direction the user is facing relative to the terrain image.

2. The method of claim 1 including the step of; activating a audio warning of the severity of the greatest threat and direction that threat is approaching.

3. The method of claim 1 including the step of; resolving possible false alarms by the methods of tracking of each moving object.

4. The method of claim 1 including the step of; transmitting and receiving the beam from a hand held unit.

5. The method of claim 1 including the step of; the communicating means comprises a backpack for mounting on the back of a user.

6. The method of claim 1 including the step of; activating a vibrator matrix on a backpack to indicated to single a user the location and distance of an object.

7. The method of claim 1 including the step of; activating an audio means to indicate overscanning of a field.

8. The method of claim 1 including the step of; the communicating the information on a CRT display.

* * * * *